US010675194B2

(12) United States Patent
Kudo et al.

(10) Patent No.: US 10,675,194 B2
(45) Date of Patent: Jun. 9, 2020

(54) ABSORBENT ARTICLE

(71) Applicant: UNICHARM CORPORATION, Ehime (JP)

(72) Inventors: Jun Kudo, Kanonji (JP); Toshiyuki Tanio, Kanonji (JP); Yuji Takahashi, Kanonji (JP); Asami Shima, Kanonji (JP); Tomoyuki Fujita, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 726 days.

(21) Appl. No.: 15/323,006

(22) PCT Filed: May 12, 2015

(86) PCT No.: PCT/JP2015/063660
§ 371 (c)(1),
(2) Date: Dec. 29, 2016

(87) PCT Pub. No.: WO2016/002350
PCT Pub. Date: Jan. 7, 2016

(65) Prior Publication Data
US 2017/0135877 A1    May 18, 2017

(30) Foreign Application Priority Data

Jun. 30, 2014    (JP) ................. 2014-135218

(51) Int. Cl.
*A61F 13/15*    (2006.01)
*A61F 13/84*    (2006.01)
(Continued)

(52) U.S. Cl.
CPC .......... *A61F 13/8405* (2013.01); *A61F 13/47* (2013.01); *A61F 13/472* (2013.01);
(Continued)

(58) Field of Classification Search
CPC .... A61F 13/8405; A61F 13/47; A61F 13/472; A61F 13/53; A61F 13/539;
(Continued)

(56) References Cited

U.S. PATENT DOCUMENTS 4,790,836 A    12/1988  Brecher
2009/0221980 A1*   9/2009  Mosbacher ............. A61F 13/42
                                                    604/385.01
(Continued)

FOREIGN PATENT DOCUMENTS

EP          1250940 A1    10/2002
JP       2002-336296 A    11/2002
(Continued)

OTHER PUBLICATIONS

Atsushi Fujita, "Prediction of Organic Compounds and Organic Conceptual Diagram", pp. 719-725, vol. 11, No. 10, Kagaku no Ryoiki (Region of Chemistry), Oct. 1957, Japan.
(Continued)

*Primary Examiner* — Jacqueline F Stephens
(74) *Attorney, Agent, or Firm* — Hauptman Ham, LLP (57) ABSTRACT

An absorbent article has a planar direction and a thickness direction. The absorbent article includes a volatile first functional component, a volatile second functional component, water-disintegrable microcapsules that contain the second functional component, and a solvent that keeps the second functional component contained inside the microcapsules. Between a liquid-permeable layer and an absorption layer, the absorbent article has functional composition coated regions that extend in the planar direction and that are coated with the functional composition, and has adhesive coated regions that extend in the planar direction and that are coated with an adhesive. The adhesive coated regions have
(Continued)

an adhesive region that directly or indirectly joins the liquid-permeable payer and the absorption layer.

12 Claims, 2 Drawing Sheets (51) Int. Cl.
| | |
|---|---|
| A61F 13/539 | (2006.01) |
| A61F 13/472 | (2006.01) |
| A61L 15/46 | (2006.01) |
| A61L 15/42 | (2006.01) |
| A61F 13/475 | (2006.01) |
| A61F 13/49 | (2006.01) |
| A61L 15/62 | (2006.01) |
| A61F 13/47 | (2006.01) |
| A61F 13/53 | (2006.01) |

(52) U.S. Cl.
CPC .......... *A61F 13/4756* (2013.01); *A61F 13/49* (2013.01); *A61F 13/53* (2013.01); *A61F 13/539* (2013.01); *A61L 15/42* (2013.01); *A61L 15/46* (2013.01); *A61L 15/62* (2013.01); *A61F 2013/530481* (2013.01); *A61F 2013/53908* (2013.01); *A61F 2013/8408* (2013.01); *A61F 2013/8414* (2013.01); *A61F 2013/8452* (2013.01)

(58) Field of Classification Search
CPC .......... A61F 2013/53908; A61F 2013/530481; A61F 2013/8408; A61F 2013/8414

USPC .......... 604/359, 360, 361, 365, 367
See application file for complete search history.

(56) References Cited

U.S. PATENT DOCUMENTS

| | | | |
|---|---|---|---|
| 2012/0089106 A1* | 4/2012 | Komatsu | ............ A61F 13/42 604/367 |
| 2012/0095424 A1 | 4/2012 | Komatsu et al. | |
| 2012/0109088 A1 | 5/2012 | Komatsu et al. | |
| 2013/0157863 A1 | 6/2013 | Hahn et al. | |
| 2014/0324004 A1* | 10/2014 | Song | ............ A61L 15/56 604/359 |

FOREIGN PATENT DOCUMENTS

| | | |
|---|---|---|
| JP | 2004-16307 A | 1/2004 |
| JP | 2007-525245 A | 9/2007 |
| JP | 2008-6277 A | 1/2008 |
| JP | 2010-234027 A | 10/2010 |
| JP | 2010-234028 A | 10/2010 |
| JP | 2010-234031 A | 10/2010 |
| WO | 98/26808 A2 | 6/1998 |
| WO | 2004/103235 A1 | 12/2004 |
| WO | 2008/120112 A1 | 10/2008 |

OTHER PUBLICATIONS

International Search Report in International Application No. PCT/JP2015/063660, dated Jun. 9, 2015.

* cited by examiner

ABSORBENT ARTICLE

RELATED APPLICATIONS

The present application is a National Phase of International Application Number PCT/JP2015/063660, filed May 12, 2015, which claims priority to Japanese Application Number 2014-135218, filed Jun. 30, 2014.

TECHNICAL FIELD

The present disclosure relates to an absorbent article.

BACKGROUND ART

Absorbent articles having an aromatic function and a cooling function are known. For example, PTL 1 describes an absorbent article comprising a cooling material that includes a refrigerant, between a front sheet and a back sheet. In the absorbent article of PTL 1, the refrigerant is protected in water-disintegratable polymer cells, the refrigerant being released after having contacted with body fluid or the like from the user.

CITATION LIST

Patent Literature

PTL 1 Japanese Unexamined Patent Publication No. 2010-234027

SUMMARY OF INVENTION

Technical Problem

With the absorbent article described in PTL 1, the refrigerant is encapsulated in water-soluble polymer cells or the like so that it exhibits its function only after it has contacted with fluid, such as body fluid, and does not exhibit its function until the user has opened the absorbent article and worn it, and it has absorbed body fluid.

It is therefore an object of the present disclosure to provide an absorbent article that can exhibit a desired function at a desired timing, and that is resistant to twisting during use.

Solution to Problem

The present inventors have devised an absorbent article including a liquid-permeable layer, a liquid-impermeable layer, an absorbing layer between the liquid-permeable layer and liquid-impermeable layer, and a functional composition, the absorbent article having a planar direction and a thickness direction, wherein the functional composition includes a volatile first functional component, a volatile second functional component, water-disintegratable microcapsules encapsulating the second functional component, and a solvent that keeps the second functional component encapsulated in the microcapsules, the absorbent article has a functional composition-coated region in which the functional composition has been coated, extending in the planar direction between the liquid-permeable layer and the absorbing layer, and an adhesive-coated region in which an adhesive has been coated, and the adhesive-coated region has an adhered region in which the liquid-permeable layer and the absorbing layer are directly or indirectly adhered.

Advantageous Effects of Invention

The absorbent article of the present disclosure can exhibit a desired function at a desired timing, and is resistant to twisting during use.

DESCRIPTION OF EMBODIMENTS

Definitions

The definitions of several of the terms used as used herein will now be explained.

[Microcapsules]

As used herein, "microcapsules" means capsules having sizes with diameters of 1 to 1,000 µm, and having spaces that encapsulate a core material (second functional component). The outer shapes of the capsules are not particularly restricted so long as they allow the core material to be encapsulated and release of the core material to be controlled, and for example, the outer shapes may be spherical, amorphous or the like. The capsules may be mononuclear having a single space for holding the core material, or polynuclear having multiple spaces for holding the core material. The shapes of the spaces may be spherical, amorphous or other spatial forms.

Examples of microcapsules are ones having a spherical outer appearance and polynuclear spaces.

[Water Disintegratability]

As used herein, "water disintegratability" is a term relating to microcapsules and refers to the property of disintegrating to an extent that releases the encapsulated second functional component upon contact with a fluid (aqueous solution), such as body fluid. Specifically, this includes cases where the material of the microcapsule dissolves in water and disintegrates when the microcapsules contact with fluid, and cases where, when the microcapsules contact with fluid, the microcapsules become imbibed with water and lose their strength, resulting in destruction of the microcapsules and disintegration.

[Wearer]

As used herein, "wearer" means the wearer of the absorbent article, and for example, the wearer may be an infant or care receiver in the case of a disposable diaper, or a female in the case of a sanitary napkin.

[User]

As used herein, "user" means the user of the absorbent article, and in addition to the wearer mentioned above, it includes any person that fits the absorbent article onto the wearer, such as a mother or caregiver in the case of disposable diaper, for example.

The absorbent article of the present disclosure will now be described in detail with reference to the accompanying drawings as necessary.

Figure 1:
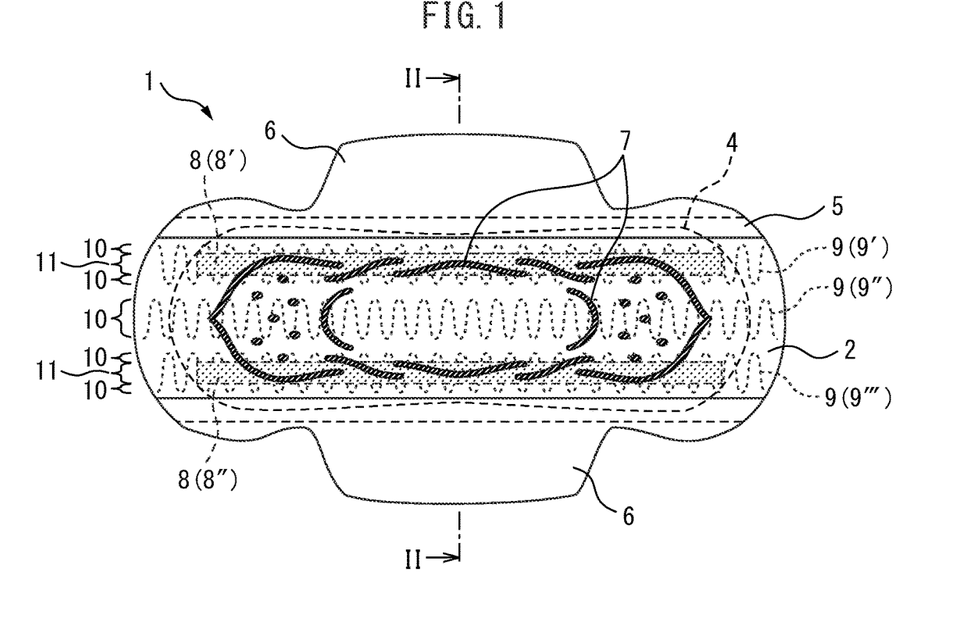
FIG. 1 is a plan view of an absorbent article according to an embodiment of the present disclosure.
Figure 2:
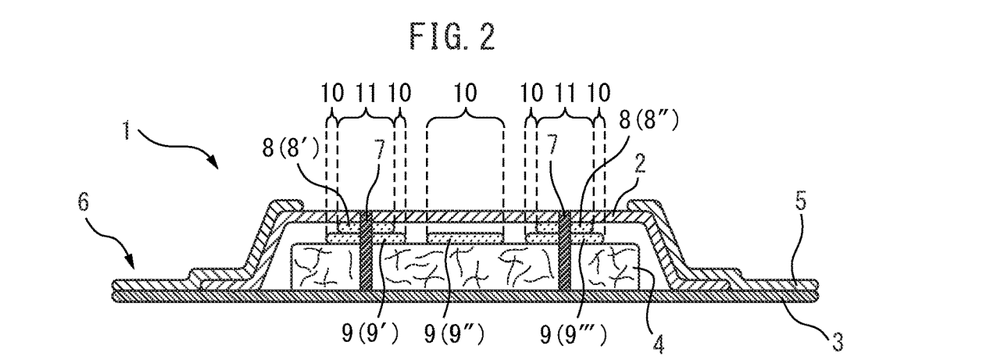
FIG. 2 is a cross-sectional view along cross-section II-II of FIG. 1.

FIG. 1 is a front view of an absorbent article, and more specifically a front view of a sanitary napkin, according to an embodiment of the disclosure. FIG. 2 is a cross-sectional view along cross-section II-II of FIG. 1.

The absorbent article 1 shown in FIG. 1 and FIG. 2 has a top sheet 2 as a liquid-permeable layer, a back sheet 3 as a liquid-impermeable layer, and an absorbent body 4 as an absorbing layer, between the top sheet 2 and back sheet 3.

It should be noted that FIG. 2 is magnified in the thickness direction of the absorbent article 1, for greater clarity of the disclosure. For example, for representation of the functional composition-coated regions 8' and 8" in FIG. 2, a space is shown between the adhesive-coated region 9''' and the top sheet 2, but in actuality the adhesive-coated region 9''' has the absorbent body 4 and the top sheet 2 adhered together.

The absorbent article 1 shown in FIG. 1 comprises a pair of side flaps 6 on both edges in the lengthwise direction of the absorbent article 1, formed from side sheets 5 and a back sheet 3, to anchor the absorbent article 1 to the clothing of the wearer, such as shorts.

The absorbent article 1 shown in FIG. 1 also has three adhesive-coated regions 9 (9', 9", 9''') coated with an adhesive and extending in the planar direction of the absorbent article 1, between the top sheet 2 and absorbent body 4. The three adhesive-coated regions 9 (9', 9", 9''') are disposed along the lengthwise direction of the absorbent article 1, at fixed intervals in the widthwise direction of the absorbent article 1. In each adhesive-coated region 9, the adhesive is disposed along the lengthwise direction of the absorbent article 1 while reciprocating (in a Z-shape) in the widthwise direction of the absorbent article 1. The three adhesive-coated regions 9 (9', 9", 9''') are also disposed in contact with the absorbent body 4.

The absorbent article 1 shown in FIG. 1 also has two functional composition-coated regions 8 (8', 8") coated with a functional composition and extending in the planar direction of the absorbent article 1, between the top sheet 2 and absorbent body 4. The functional composition-coated regions 8' and 8" are each disposed in a sheet-like manner between the top sheet 2 and absorbent body 4, in contact with the adhesive-coated regions 9' and 9'''. The functional composition-coated regions 8' and 8" are also disposed in contact with the top sheet 2. The composition of the functional composition is described below.

The adhesive-coated region 9''' has a adhered region 10 where it is directly adhered with the top sheet 2 and absorbent body 4. Also, each of the adhesive-coated regions 9' and 9''' has a adhered region 10 where they are directly adhered with the top sheet 2 and absorbent body 4, and a microcapsule-holding region 11.

The adhered regions 10 are not adhered with the functional composition-coated regions 8, and more specifically, the adhered regions 10 adhere the top sheet 2 and absorbent body 4 without including a solvent as a component of the functional composition.

In the microcapsule-holding regions 11, the adhesive having a pressure-sensitive adhesive property holds microcapsules forming the functional composition.

The absorbent article 1 shown in FIG. 1 has a plurality of embossed sections 7, formed by embossing the top sheet 2 and absorbent body 4 in a manner sandwiching the functional composition-coated regions 8, the embossed sections 7 holding the second functional component encapsulated in the microcapsules in the regions where those sections overlap with the functional composition-coated regions 8 in the thickness direction of the absorbent article 1.

In the embodiment illustrated in FIG. 1 and FIG. 2, the adhesive-coated regions 9 are formed by coating the adhesive in the lengthwise direction of the absorbent article 1 while reciprocating in the widthwise direction of the absorbent article 1, but for the absorbent article of the present disclosure the adhesive-coated region is not restricted to this, and may be disposed in any form that is known in the technical field. For example, the adhesive-coated region may be disposed along the lengthwise direction or widthwise direction of the absorbent article in a spiral form, Z-shape, linear form or dotted form.

In the embodiments shown in FIG. 1 and FIG. 2, the functional composition-coated regions 8 are disposed in a sheet-like manner on the adhesive-coated regions 9 at both edges in the lengthwise direction of the absorbent article 1, but for the absorbent article of the present disclosure, the arrangement of the functional composition-coated regions 8 are not limited to those shown in FIG. 1 and FIG. 2. For example, the functional composition-coated region may be disposed along the lengthwise direction or widthwise direction of the absorbent article, in a sheet-like form, linear form, spiral form, Z-shape, linear form, dotted form, or the like. The functional composition-coated region may also be disposed at the center in the lengthwise direction of the absorbent article, and disposed at both edges in the lengthwise direction of the absorbent article.

In the absorbent article of the disclosure, the functional composition-coated region is a region in which the functional composition has been coated.

The functional composition includes a first functional component, a second functional component, water-disintegratable microcapsules encapsulating the second functional component, and a solvent.

The solvent, depending on its viscosity, may migrate into a liquid-permeable layer, absorbing layer or, if desired, an auxiliary sheet layer, by the action of capillary movement.

[First Functional Component and Second Functional Component]

The respective functions of the first functional component and second functional component are not particularly restricted so long as they are functions that provide comfort for the user compared to when those components are not present, and examples include functions selected from the group consisting of aromatic functions, cooling functions, deodorant functions, antibacterial functions, skin care functions, and any combination thereof.

As used herein, the first functional component and/or second functional component may be collectively referred to simply as "functional components".

Functional components with an aromatic function are not particularly restricted so long as they are used as aromatics in the technical field, and examples include highly volatile aromatics with boiling points of no higher than about 250° C., and moderately volatile aromatics with boiling points of about 250° C. to about 300° C.

Functional components with aromatic functions may collectively be referred to as "aromatic components".

Examples of highly volatile aromatics include anisole, benzaldehyde, benzyl acetate, benzyl alcohol, benzyl formate, isobornyl acetate, citronellal, citronellol, citronellyl acetate, paracymene, decanal, dihydrolinalool, dihydromyrcenol, dimethylphenylcarbinol, eucalyptol, l-carvone, geranial, geraniol, geranyl acetate, geranylnitrile, nerol, neryl acetate, nonyl acetate, linalool, linalyl acetate, phenylethyl alcohol, α-pinene, β-pinene, γ-pinene, α-ionone, β-ionone, γ-ionone, α-terpineol, β-terpineol, terpinyl acetate and tentarome.

Examples of moderately volatile aromatics include amylcinnamaldehyde, methyl dihydrojasmonate, isoamyl salicylate, β-caryophyllene, cedrene, cedryl methyl ether, cinnamic alcohol, coumarin, dimethylbenzyl carbinyl acetate, ethylvanillin, eugenol, isoeugenol, γ-methylionone, heliotropin, hexyl salicylate, cis-3-hexenyl salicylate, phenylhexanol, vanillin and pentalide.

These aromatic components contain aromatics with green herbal fragrances. Aromatics with green herbal fragrances can safely and conveniently alleviate concomitant symptoms of menstrual discharge, and particularly symptoms creating psychological discomfort, without producing physical stimulation to the body and without oral administration, and they provide a comfortable feel for the user.

The aforementioned green herbal fragrances are incense tones including green fragrances (green notes) or herbal fragrances (herbal notes). Green fragrances are the refreshing incense tones of grass or young leaves. Herbal fragrances (herbal notes) are incense tones characteristically having natural, medicinal fragrances obtained using herbs.

Examples of aromatics having green herbal fragrances include cis-3-hexenol, cis-3-hexenyl formate, cis-3-hexenyl acetate, cis-3-hexenyl propionate, cis-3-hexenyl butyrate, trans-2-hexenal, trans-2-hexenyl acetate, hexyl acetate, styrallyl acetate, 2-methyl-3-(3,4-methylenedioxyphenyl)-propanal (Helional, by IFF), 3(4)-(5-ethylbicyclo[2,2,1]heptyl-2)-cyclohexanol, 2-pentyloxyallyl glycolate (Allylamyl glycolate, by IFF), 4-methyl-3-decen-5-ol (Undecavertol, by Givaudan), hexylaldehyde, 2,4-dimethyl-3-cyclohexenylcarboxyaldehyde (Tripral, by IFF) and phenylacetaldehyde.

Aromatics having green herbal fragrances include 1-menthol, 1,8-cineol, methyl salicylate, citronellal, camphor, borneol, isobornyl acetate, terpinyl acetate, eugenol, anethole, 4-methoxybenzyl alcohol and estragole.

Functional components having cooling functions (functional components having cooling functions will also be referred to collectively as "cooling components") include those known as cooling materials in the technical field, and examples include components that act on receptor activated channels in skin nerves (TRPM8), such as menthol (for example, 1-menthol) and its derivatives, methyl salicylate, camphor, and essential oils derived from plants (such as mint or *eucalyptus*). In addition, functional components having such a cooling function include components that lower the surrounding temperature by heat of vaporization, including alcohols, such as methanol and ethanol.

Functional components having the deodorant functions (functional components with deodorant functions will also be referred to collectively as "deodorant components") include those known as deodorants in the technical field.

Examples of the skin care functions include anti-inflammatory functions, antipruritic functions, eruption-preventing functions and moisturizing functions, and examples of functional components with the skin care functions include menthol and methyl salicylate.

Functional components with the skin care functions may also be referred to collectively as skin care components, and functional components having anti-inflammatory functions, antipruritic functions, eruption-preventing functions and moisturizing functions may be referred to collectively as anti-inflammatory components, antipruritic components, eruption-preventing components and moisturizing components, respectively.

The first functional component and the second functional component both have a volatile property.

The volatile property is one with a preferred vapor pressure that will differ depending on the function to be exhibited by the functional component, and for example, the first functional component and second functional component have a vapor pressure of preferably 30 Pa or greater, more preferably 50 Pa or greater and even more preferably 70 Pa or greater at 25° C., 1 atmosphere. If the vapor pressure is too low, it will tend to be difficult to exhibit the desired function, and if the vapor pressure is too high, the functional component may volatilize off before the user uses the absorbent article, sometimes resulting in its amount being reduced or its function being over-exhibited on the skin of the wearer.

[Microcapsules]

The water-disintegratable microcapsules are components that hold the second functional component on the inner side, and upon contacting with fluid, such as body fluid, they disintegrate and release the second functional component to the exterior. The released second functional component gasifies by body heat of the wearer, exhibiting its function to the skin of the wearer.

The degree of water disintegratability of the microcapsules will differ depending on how the second functional component is to be released after contacting with the fluid, and for example, higher water disintegratability is preferred for rapid release of the second functional component after contacting with fluid, while lower water disintegratability is preferred for sustained release of the second functional component.

When the microcapsules in the absorbent article of the disclosure disintegrate by dissolution in water, the microcapsules have a water solubility in the range of preferably 10 to 300 g, more preferably 20 to 200 g and even more preferably 30 to 100 g, in 100 g of water at 25° C.

The water solubility is measured according to the flask method of OECD Guidelines No. 105, except that the testing temperature is set at 25° C.

The microcapsules are preferably insoluble in the solvent used as the dispersing medium for the microcapsules, and preferably they do not swell in the solvent used as the dispersing medium for the microcapsules. This is from the viewpoint of protecting the second functional component encapsulated in them.

For example, the microcapsules may have a solvent solubility of preferably no greater than 1.0 g, more preferably no greater than 0.5 g and even more preferably no greater than 0.1 g, in 100 g of solvent as the dispersing medium of the microcapsules, at 25° C.

The solvent solubility is evaluated by adding 1.0 g (or, 0.5 g, 0.1 g) of sample to 100 g of solvent at 25° C., allowing the mixture to stand for 24 hours and gently stirring if necessary, and then visually evaluating whether or not the sample has dissolved.

The material for such microcapsules may be, for example, a saccharide, such as a monosaccharide (for example, glucose), disaccharide (for example, sucrose), polysaccharide (for example, dextrin, glucomannan, sodium alginate or water-soluble starch), gelatin, a water-soluble polymer (for example, polyvinyl alcohol or polyvinyl acetate), or the like.

The microcapsules include microcapsules that pass through a sieve with a mesh opening of 75 μm and remain on a sieve with a mesh opening of 45 μm, at preferably 50 mass % or greater and more preferably 70 mass % or greater. This is from the viewpoint of the dispersibility of the microcapsules in the solvent, and coatability.

Such microcapsules are commercially available, such as INCAP™ marketed by Symrise, for example.

The microcapsules also form an aqueous solution when the material of the microcapsules dissolves in water, the second functional component and surfactant becoming mixed in the aqueous solution, allowing production by reduced pressure drying while spraying the aqueous solution.

[Solvent]

The solvent preferably holds the second functional component encapsulated in the microcapsules and also holds the first functional component, or in other words, it preferably dissolves the first functional component but does not dissolve or swell the microcapsules.

The solvent used to disperse the microcapsules may be referred to as the "first solvent", in order to distinguish it from the second solvent that can be encapsulated in the microcapsules, as described below.

From the viewpoint of avoiding disintegration of the water-disintegratable microcapsules, the solvent is preferably a lipophilic solvent.

From the viewpoint of lipophilicity, the solvent has an IOB, described hereunder, of 0.00 or greater, and preferably no greater than 1.0, more preferably no greater than 0.8 and even more preferably no greater than 0.6.

The IOB (Inorganic Organic Balance) is an indicator of the hydrophilic-lipophilic balance, and as used herein, it is the value calculated by the following formula by Oda et al.:

IOB=Inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
| --- | --- | --- |
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

In addition, the solvent preferably has a kinematic viscosity of 0.01 to 80 $mm^2/s$ at 40° C., from the viewpoint of coatability of the functional composition.

The kinematic viscosity is measured according to JIS K 2283:2000, "5. Kinematic Viscosity Test Method", using a Cannon-Fenske reverse-flow viscometer, at a testing temperature of 40° C.

The solvent has a vapor pressure of preferably 0.00 to 0.01 Pa, more preferably 0.000 to 0.001 Pa and even more preferably 0.0000 to 0.0001 Pa at 1 atmosphere, 25° C. Considering that the absorbent article of the disclosure is to be used in contact with the human body, the solvent has a vapor pressure of preferably 0.00 to 0.01 Pa, more preferably 0.000 to 0.001 Pa and even more preferably 0.0000 to 0.0001 Pa at 1 atmosphere, 40° C. If the vapor pressure is high, gasification may occur during storage and the amount of solvent and first functional component may be reduced, often creating problems, such as odor during wear.

Examples of solvents include lipophilic alcohol-based solvents, ester-based solvents, ether-based solvents, ketone-based solvents and hydrocarbon-based solvents.

An example of the hydrocarbon-based solvent is liquid paraffin, and an example of the ester-based solvent is isopropyl myristate.

The solvent may further include components having an IOB of 0.00 to 0.60, a kinematic viscosity of 0.01 to 80 $mm^2/s$ at 40° C., a water holding percentage of 0.01 to 4.0 mass % and a weight-average molecular weight of less than 1,000 (these may collectively be referred to as "body fluid lubricity imparting agent").

The body fluid lubricity imparting agent is the same component as the "blood modifying agent" described in International Patent Publication No. WO2012/133724, previously filed by the present applicant, and is likewise the same component as the "blood slipping agent" described in International Patent Publication No. WO2013/129236, also by the present applicant.

If the solvent includes a body fluid lubricity imparting agent, it will be possible for body fluid that has reached the liquid-permeable layer to rapidly slip down into the absorbent body over long periods of time.

Examples of body fluid lubricity-imparting materials include triglycerides, such as PANACET 810s and PANACET 800 by NOF Corp., and hydrocarbons, such as PARLEAM 6 by NOF Corp.

The solvent may include components selected from the group consisting of PPG-4 butyl ether, PPG-12 butyl ether, PPG-17 butyl ether, PPG-20 butyl ether, PPG-24 butyl ether, PPG-33 butyl ether, PPG-40 butyl ether, PPG-52 butyl ether, PPG-3 myristyl ether, PPG-10 cetyl ether, PPG-11 stearyl ether, PPG-15 stearyl ether, PPG-2 lanolin alcohol ether, PPG-5 lanolin alcohol ether, PPG-10 lanolin alcohol ether, PPG-20 lanolin alcohol ether, PPG-26 oleate, PPG-36 oleate, PPG-5.5 castorate, PPG-6 glyceryl ether, PPG-8 glyceryl ether, PPG-10 glyceryl ether, PPG-16 glyceryl ether, PPG-9 diglyceryl ether, PPG-14 diglyceryl ether, PPG-25 sorbitol and PPG-33 sorbitol, as well as any combination thereof.

The solvent may also include components selected from the group consisting of PPG-30 cetyl ether, PPG-15 isohexadecyl ether, PPG-4 lauryl ether, PPG-20 distearate, PPG-12 dilaurate, PPG-15 dicocoate, PPG-10 cetyl phosphate, PPG-9 laurate, PPG-8 dioctate, PPG-15 stearate, PPG-8 diethyl hexylate, PPG-10 glyceryl stearate, PPG-2 cocamide, PPG-10 tallow amine, PPG-10 oleamide, PPG-5 sucrose cocoate, PPG-20 methylglucose ether distearate, PPG-20 methylglucose ether acetate, PPG-20 sorbitan tristearate, PPG-20 methylglucose ether distearate, PPG-15 stearyl ether benzoate, PPG-10 sorbitan monostearate, PPG-10 hydrogenated castor oil, PPG-10 cetyl ether phosphate, PPG-10 dinonyl phenolate, PPG-7 lauryl ether, PPG-5 lanolin wax ether, PPG-5 lanolin wax, PPG-4 jojoba alcohol ether, PPG-3 myristyl ether propionate, PPG-3 benzyl ether myristate, PPG-3 hydrogenated castor oil, PPG-3-hydroxyethylsoyamide, PPG-2 lanolin alcohol ether and PPG-1 coconut fatty acid isopropanolamide, as well as any combination thereof.

[Functional Composition]

The mechanism by which the functional composition in the functional composition-coated region of the absorbent article of the disclosure exhibits the desired function at the desired timing is as follows.

When the user unseals the absorbent article, the first functional component dissolved in the solvent (first solvent) volatilizes, and the function of the first functional component is exhibited for the user. For example, when the first functional component is an aromatic component, the user senses an ambient drifting aroma.

When the first functional component is a deodorant component, and the user unseals the absorbent article, the first functional component exhibits its deodorant function and the user is less likely to sense the odor from the fluid absorbed by an absorbent article that requires exchanging.

The amount of release of the first functional component can be varied by the amount of the first functional component and the vapor pressure of the first functional component.

For example, the first functional component can be released to the surrounding area at a high concentration in a short period of time by increasing the amount of the first functional component in the absorbent article or by selecting a first functional component with a high vapor pressure.

By selecting a first functional component with a low vapor pressure, for example, on the other hand, the first functional component can be released into the surrounding area over a long period of time.

When the absorbent article is to be sold as a package of individually packaged absorbent articles, the form of the individual packages and the packaged form may be adjusted; for example, the absorbent articles may be individually packaged with air permeable nonwoven fabrics, and the multiple individually packaged absorbent articles packaged with a polymer film to allow the function of the first functional component to be exhibited after the user has opened the package.

When the absorbent article is then worn by the wearer, the body heat of the wearer promotes gasification of the first functional component so that the function of the first functional component is promoted. For example, when the first functional component is an aromatic component, cooling component, deodorant component, antibacterial component or skin care component, this will promote the aromatic function, cooling function, deodorant function, antibacterial function or skin care function, respectively.

When the absorbent article then absorbs fluid, the absorbed fluid disintegrates the water-disintegratable microcapsules, causing release of the second functional component from the microcapsules so that its function is exhibited. For example, when the second functional component is an aromatic component, cooling component, deodorant component, antibacterial component or skin care component, this will allow the aromatic function, cooling function, deodorant function, antibacterial function or skin care function, respectively, to be exhibited.

The amount of release of the second functional component may be varied depending on the amount of the second functional component, the vapor pressure of the second functional component, the solubility of the microcapsules in water, the thickness of the microcapsule layer, and the particle sizes of the microcapsules.

For example, the second functional component can be released into the surrounding area at high concentration in a short period of time, by increasing the amount of the second functional component in the absorbent article, by selecting a second functional component with a high vapor pressure, by selecting the material of the microcapsules to be one with high solubility in water, by reducing the thickness of the microcapsule layer, or by reducing the particle sizes of the microcapsules.

Also, the second functional component can be released in a sustained manner, for example, by decreasing the amount of the second functional component in the absorbent article, by selecting a second functional component with a low vapor pressure, by selecting the material of the microcapsules to be one with low solubility in water, by increasing the thickness of the microcapsule layer, or by increasing the particle sizes of the microcapsules.

From the viewpoint of controlling the release property of the second functional component, the microcapsules may further include a solvent in addition to the second functional component (this solvent will also be referred to hereunder as the "second solvent").

The second solvent may be any of the same ones mentioned for the first solvent.

The amount of the first functional component in the functional composition will differ depending on the function of the first functional component, but generally speaking the functional composition includes the first functional component in a proportion of preferably 0.01 to 20 mass %, more preferably 0.05 to 15 mass % and even more preferably 0.1 to 10 mass %.

The functional composition includes the second functional component-containing microcapsules in a proportion of preferably 0.1 to 60 mass %, more preferably 5 to 40 mass % and even more preferably 10 to 30 mass %. This is from the viewpoint of the coatability of the functional composition.

The amount of the second functional component in the functional composition will differ depending on the function of the second functional component, but generally speaking the functional composition includes the second functional component in a proportion of preferably 0.01 to 30 mass %, more preferably 0.05 to 20 mass % and even more preferably 1 to 15 mass %.

[Absorbent Article]

In the functional composition-coated region of the absorbent article of the disclosure, the basis weight of the functional composition will vary depending on the concentration of the functional components, but it is preferably 1 to 12 $g/m^2$ and more preferably 2 to 10 $g/m^2$. If the basis weight is lower than 1 $g/m^2$, the functional component may be less able to exhibit its function, and if the basis weight is higher than 12 $g/m^2$, the solvent (first solvent) may inhibit adhering by the adhesive.

The adhesive-coated region in the absorbent article of the disclosure have an adhered region where the liquid-permeable layer and the absorbing layer are directly or indirectly adhered in the thickness direction of the absorbent article. The absorbent article is therefore resistant to twisting during use. The adhered region preferably do not include the solvent composing the functional composition. This is because the solvent tends to inhibit the direct or indirect adhering of the liquid-permeable layer and the absorbing layer by the adhesive.

As used herein, "the adhered region does not include the solvent composing the functional composition" means that the adhesive composing the adhered region includes the solvent in an amount of 0 to 5 mass %.

Also, in an absorbent article according to one embodiment of the disclosure, the adhesive-coated region further has a microcapsule-holding region that holds the microcapsules, as shown in FIG. 1 and FIG. 2. Since the microcapsule-holding region holds the microcapsules in this embodiment, the position of the second functional component is less likely to shift during use.

The adhesive forming the adhesive-coated region may be an adhesive that is known in the technical field, such as a hot-melt adhesive.

If microcapsule-holding region is present on the non-skin contact surface of the liquid-permeable layer, fluid that has passed through the liquid-permeable layer will be able to reach the microcapsules more rapidly, thereby allowing the second functional component to be released with a smaller amount of fluid.

The absorbent article according to several other embodiments of the disclosure has, sandwiching the functional composition-coated region, an embossed section formed by embossing at least the liquid-permeable layer and absorbing layer, as shown in FIG. 1 and FIG. 2. The solvent composing the functional composition in the functional composition-coated region tends to inhibit direct or indirect adhering between the liquid-permeable layer and the absorbing layer by the adhesive. If the absorbent article has embossed section, then adhering between the liquid-permeable layer and the absorbing layer will be stronger, and the absorbent article will be less likely to twist during use.

According to one of the embodiments, the embossed section holds the second functional component encapsulated in the microcapsules. This will allow the microcapsules, and thus the second functional component, to be continuously held at a specific position. In addition, since the embossed section has high fiber density, the fluid will tend to be preferentially guided toward the embossed section, thereby allowing the second functional component to be released with a small amount of fluid.

An absorbent article according to another embodiment of the disclosure includes a super absorbent material in the absorbing layer. For this embodiment, the super absorbent material holds the solvent composing the functional composition in its surrounding area and adsorbs it, and therefore the absorbed fluid easily contacts with the microcapsules and the microcapsules readily dissolve.

Examples of high-water-absorbing materials include starch-based, cellulosic and synthetic polymer-based high-water-absorbing materials. Examples of starch-based or cellulosic high-water-absorbing materials include starch-acrylic acid (acrylate) graft copolymer, saponified starch-acrylonitrile copolymer and crosslinked sodium carboxymethyl cellulose, and examples of synthetic polymer-based high-water-absorbing materials include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulosic high water-absorbent resins, among which polyacrylic acid salt-based (especially sodium polyacrylate-based) high water-absorbent resins are preferred.

The first functional component and second functional component in the absorbent article of the disclosure may be selected in light of any desired considerations. For example, by selecting the first functional component from among aromatic components and the second functional component from among cooling components, the wearer will be provided with an aroma after the absorbent article has been opened, and the wearer will also be provided with a cool feel after absorption of body fluid. Moreover, since night-use absorbent articles have larger sizes they tend to be stuffy when worn, but if a cooling component is used as the second functional component, the wearer will be less likely to experience discomfort.

By selecting the first functional component and second functional component from among different aromatic components, the functional component can be used as an indicator material that notifies the user, and particularly a mother or caregiver for the disposable diaper, that body fluid has been absorbed.

In addition, if the first functional component and second functional component are selected from among the same aromatic components, then their amounts can be changed to accentuate the aroma. For example, prior to absorption of fluid, a faint aroma from the first functional component will drift, and after the fluid has been absorbed, the same aroma, but stronger than before absorption of the fluid, will drift from the second functional component.

Moreover, if a deodorant component, or an aromatic component, and preferably an aromatic component with a powerful aroma, is used as the second functional component, it will be possible to use the functional component as an aroma masking material.

Figure 3:
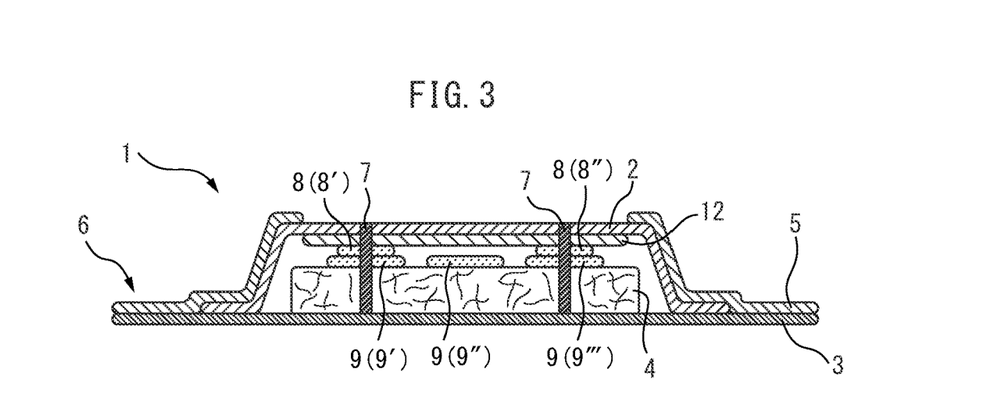
FIG. 3 is a cross-sectional view of an absorbent article according to another embodiment of the disclosure.

FIG. 3 is a cross-sectional view of an absorbent article according to another embodiment of the disclosure. FIG. 3 corresponds to cross-section II-II of FIG. 1. The absorbent article 1 shown in FIG. 3 includes an auxiliary sheet 12 between the top sheet 2 and the absorbent body 4, the functional composition-coated regions 8 being formed between the auxiliary sheet 12 and the absorbent body 4. In the absorbent article 1 shown in FIG. 3, the adhesive-coated regions 9 are disposed between the auxiliary sheet 12 and the absorbent body 4, specifically in contact with the absorbent body 4. Explanation of the other sections will be omitted since they are similar to the embodiments shown in FIG. 1 and FIG. 2.

In the embodiment shown in FIG. 3, an auxiliary sheet layer is added between the functional composition and the wearer, and therefore the function of the functional component on the skin of the wearer tends to be more subdued.

The material of the auxiliary sheet may be the same as the top sheet, such as a nonwoven fabric.

In the embodiment shown in FIG. 3, both the functional composition-coated regions and the adhesive-coated regions are disposed between the auxiliary sheet layer and the absorbing layer, but in an absorbent article according to a different embodiment of the disclosure, the functional composition-coated region and/or the adhesive-coated region are disposed between the liquid-permeable layer and an auxiliary sheet layer. This will facilitate dissolution of the microcapsules by absorbed fluid, so that the second functional component will be more easily released.

[Production of Absorbent Article]

The functional composition described above is formed by adding the first functional component, and the microcapsules that are to encapsulate the second functional component, into the solvent and mixing them. The microcapsules that are to encapsulate the second functional component may be commercially available or formed as described above.

The functional composition can be coated using a coating machine known in the technical field, such as a roll-type coating machine, curtain-type coating machine, slit-type coating machine, spray-type coating machine, dip-type coating machine, bead-type coating machine, flexo-type coating machine or gravure-type coating machine.

The functional composition is preferably coated with a contact-type coating machine having the exit nozzle for the functional composition in contact with the surface to be coated. This is to allow the functional composition to be situated at the desired positions, i.e. the functional composition-coated region to be situated at the desired positions, without scattering of the functional composition.

Contact-type coating machines include roll-type coating machines, slit-type coating machines, dip-type coating machines, bead-type coating machines, flexo-type coating machines and gravure-type coating machines.

A production example for an absorbent article, including an example of coating the functional composition, will now be explained with reference to the coating example shown in FIG. 4.

(i) A hot-melt gun (not shown) is used to coat an adhesive onto the top sheet 2 as a liquid-permeable layer, forming adhesive-coated regions 9 on the top sheet 2.

(ii) A coater 13 is used to coat the top sheet 2 with a functional composition sandwiching the adhesive-coated regions 9, forming functional composition-coated regions 8 on the top sheet 2 and adhesive-coated regions 9.

(iii) An absorbent body (not shown) is stacked on the top sheet 2, sandwiching the adhesive-coated regions 9 and functional composition-coated regions 8, to form a stacked body.

(iv) The stacked body is passed through a pair of embossing rolls (not shown), and the top sheet 2 and absorbent body 4 are embossed in a manner sandwiching the functional composition-coated regions 8, forming embossed sections (not shown).

(v) A back sheet (not shown) is stacked on the absorbent body 4, and its periphery is embossed to form an absorbent article.

In (ii), the functional composition may be coated separately for the first functional component and second functional component. For example, a coating solution containing the first functional component and a solvent, and a coating solution containing the second functional component-containing microcapsules and a solvent, may be ejected from separate nozzles to form the functional composition-coated regions 8 on the top sheet 2 and adhesive-coated regions 9.

This production example is one with the positions of the adhesive-coated regions 9 and the functional composition-coated regions 8 reversed from those of the absorbent article 1 shown in FIG. 1.

That is, for production of the absorbent article 1 shown in FIG. 1, the step of forming the adhesive-coated regions 9 and the step of forming the functional composition-coated regions 8 may simply be exchanged.

Examples for the absorbent article of the disclosure include sanitary napkins, panty liners, disposable diapers and urine-absorbing pads.

EXAMPLES

The present disclosure will now be explained in fuller detail by an example, with the understanding that the disclosure is not meant to be limited to the example.

Example 1

INCAP MENTHOL/IPM by Symrise was prepared as microcapsules for encapsulation of the second functional component. The INCAP MENTHOL/IPM contained a cooling component (menthol) as the second functional component, and the microcapsule material was material-modified starch.

A solvent containing an aromatic component as the first functional component was prepared. The solvent was IPM (isopropyl myristate).

The microcapsules and the solvent were mixed in a mass ratio of 50:50 to prepare functional composition No. 1.

Figure 4:
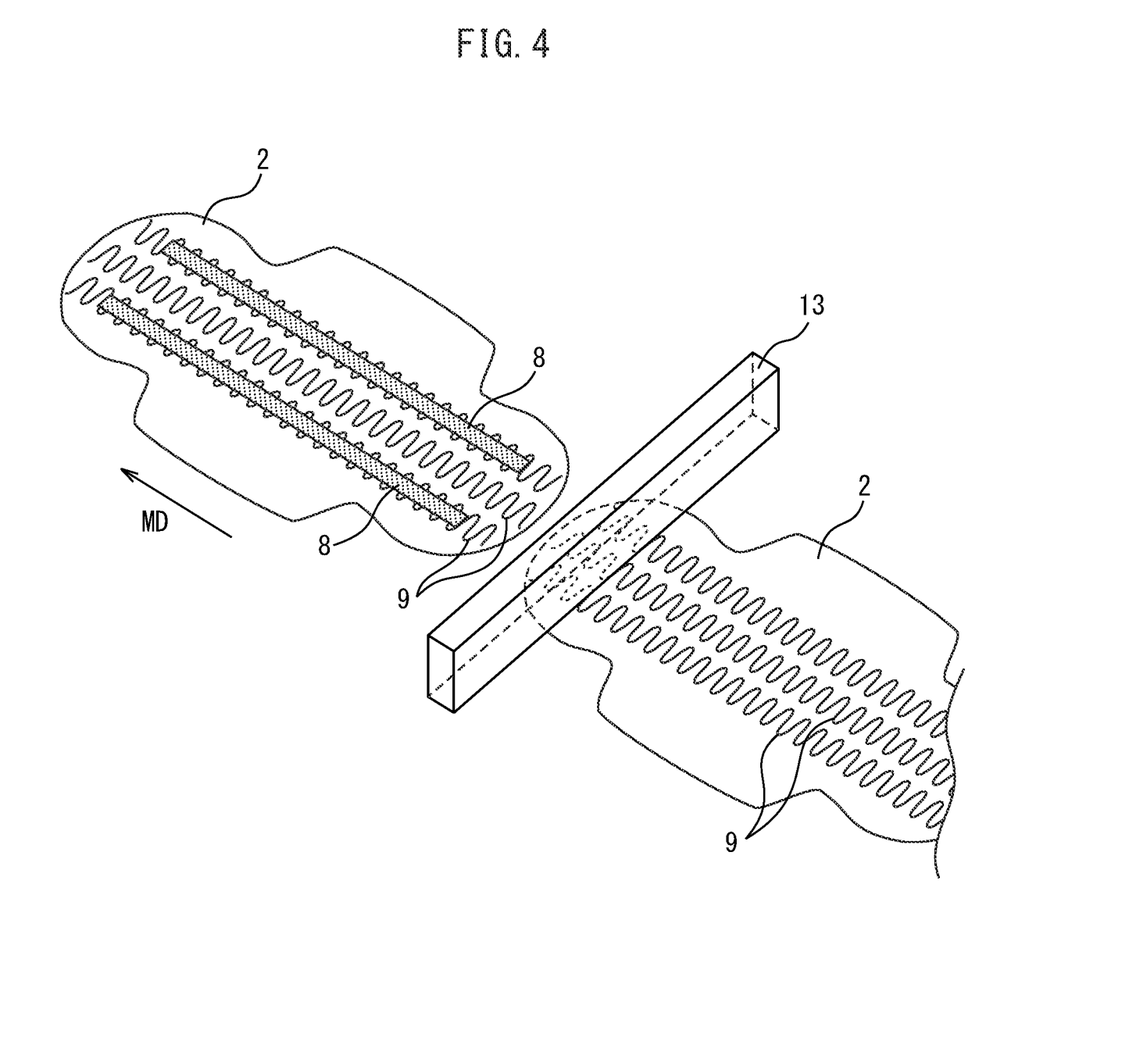
FIG. 4 is a diagram illustrating an example of production steps for the absorbent article of the disclosure.

The production steps shown in FIG. 4 were employed to produce a sanitary napkin No. 1 as shown in FIG. 1, and then sanitary napkin No. 1 was individually packaged with a polyethylene film.

The basis weight of the functional composition in the functional composition-coated regions was 4 g/m$^2$.

When sanitary napkin No. 1 was used by volunteer subjects, it was reported that the fragrant aroma from sanitary napkin No. 1 drifted after opening of the individual package and during fitting, and that after sanitary napkin No. 1 had absorbed menstrual blood, a cool sensation was felt in the region contacting with absorbent article No. 1.

Specifically, the present disclosure relates to the following aspects J1 to J11.

[J1]

An absorbent article including a liquid-permeable layer, a liquid-impermeable layer, an absorbing layer between the liquid-permeable layer and liquid-impermeable layer, and a functional composition, the absorbent article having a planar direction and a thickness direction, wherein the functional composition includes a volatile first functional component, a volatile second functional component, water-disintegratable microcapsules encapsulating the second functional component, and a solvent that keeps the second functional component encapsulated in the microcapsules, the absorbent article has a functional composition-coated region in which the functional composition has been coated, extending in the planar direction between the liquid-permeable layer and the absorbing layer, and an adhesive-coated region in which an adhesive has been coated, and the adhesive-coated region has an adhered region in which the liquid-permeable layer and the absorbing layer are directly or indirectly adhered.

[J2]

The absorbent article according to J1, wherein the adhesive-coated region has a microcapsule-holding region holding the microcapsules.

[J3]

The absorbent article according to J1 or J2, wherein the adhered region does not include the solvent.

[J4]

The absorbent article according to any one of J1 to J3, wherein the absorbent article has an embossed section formed by embossing at least the liquid-permeable layer and the absorbing layer sandwiching the functional composition-coated region, the embossed section holding the microcapsules and the second functional component.

[J5]

The absorbent article according to any one of J1 to J4, wherein the solvent has an IOB of 0.00 to 0.60, a kinematic viscosity of 0.01 to 80 mm$^2$/s at 40° C., and a vapor pressure of 0.00 to 0.01 Pa at 1 atmosphere, 25° C.

[J6]

The absorbent article according to any one of J1 to J5, wherein the absorbing layer includes a super absorbent material.

[J7]

The absorbent article according to any one of J1 to J6, wherein the first functional component and the second functional component each have a function selected from the group consisting of aromatic functions, cooling functions, deodorant functions, antibacterial functions, skin care functions, and any combination thereof.

[J8]

The absorbent article according to any one of J1 to J7, wherein the second functional component has a cooling function.

[J9]

The absorbent article according to any one of J1 to J8, wherein the first functional component has an aromatic function.

[J10]

The absorbent article according to any one of J1 to J9, wherein the absorbent article includes an auxiliary sheet layer between the liquid-permeable layer and the absorbing layer, and the functional composition-coated region are formed between the liquid-permeable layer and the auxiliary sheet layer or between the auxiliary sheet layer and the absorbing layer.

[J11]

The absorbent article according to J10, wherein the adhesive-coated region is formed between the liquid-permeable layer and the auxiliary sheet or between the auxiliary sheet and the absorbing layer.

REFERENCE SIGNS LIST

1 Absorbent article
2 Top sheet
3 Back sheet
4 Absorbent body
5 Side sheet
6 Side flap
7 Embossed section
8 Functional composition-coated region
9 Adhesive-coated region
10 Adhered region
11 Microcapsule-holding region
12 Auxiliary sheet
13 Coater

The invention claimed is:

1. An absorbent article including a liquid-permeable layer, a liquid-impermeable layer, an absorbing layer between the liquid-permeable layer and liquid-impermeable layer, and a functional composition, the absorbent article having a planar direction and a thickness direction,
   wherein the functional composition includes a volatile first functional component, a volatile second functional component, water-disintegratable microcapsules encapsulating the second functional component, and a solvent that keeps the second functional component encapsulated in the microcapsules,
   the absorbent article has a functional composition-coated region in which the functional composition has been coated, extending in the planar direction between the liquid-permeable layer and the absorbing layer, and an adhesive-coated region in which an adhesive has been coated, and
   the adhesive-coated region has an adhered region in which the liquid-permeable layer and the absorbing layer are directly or indirectly adhered.

2. The absorbent article according to claim 1, wherein the adhesive-coated region has a microcapsule-holding region holding the microcapsules.

3. The absorbent article according to claim 1, wherein the adhered region does not include the solvent.

4. The absorbent article according to claim 1, wherein the absorbent article has an embossed section formed by embossing at least the liquid-permeable layer and the absorbing layer sandwiching the functional composition-coated region, the embossed section holding the microcapsules and the second functional component.

5. The absorbent article according to claim 1, wherein the solvent has an IOB of 0.00 to 0.60, a kinematic viscosity of 0.01 to 80 mm$^2$/s at 40° C., and a vapor pressure of 0.00 to 0.01 Pa at 1 atmosphere, 25° C.

6. The absorbent article according to claim 1, wherein the absorbing layer includes a super absorbent material.

7. The absorbent article according to claim 1, wherein the first functional component and the second functional component each have a function selected from the group consisting of aromatic functions, cooling functions, deodorant functions, antibacterial functions, skin care functions, and any combination thereof.

8. The absorbent article according to claim 1, wherein the second functional component has a cooling function.

9. The absorbent article according to claim 1, wherein the first functional component has an aromatic function.

10. The absorbent article according to claim 1, wherein the absorbent article includes an auxiliary sheet layer between the liquid-permeable layer and the absorbing layer, and the functional composition-coated region are formed between the liquid-permeable layer and the auxiliary sheet layer or between the auxiliary sheet layer and the absorbing layer.

11. The absorbent article according to claim 10, wherein the adhesive-coated region is formed between the liquid-permeable layer and the auxiliary sheet or between the auxiliary sheet and the absorbing layer.

12. An absorbent article including a liquid-permeable layer, a liquid-impermeable layer, an absorbing layer between the liquid-permeable layer and liquid-impermeable layer, and a functional composition, the absorbent article having a planar direction and a thickness direction,
   wherein the functional composition includes a volatile functional component, water-disintegratable microcapsules encapsulating the functional component, and a solvent that keeps the functional component encapsulated in the microcapsules,
   the absorbent article has a functional composition-coated region in which the functional composition has been coated, extending in the planar direction between the liquid-permeable layer and the absorbing layer, and an adhesive-coated region in which an adhesive has been coated, and
   the adhesive-coated region has an adhered region in which the liquid-permeable layer and the absorbing layer are directly or indirectly adhered.

* * * * *